United States Patent [19]

Murase et al.

[11] Patent Number: 4,970,214

[45] Date of Patent: Nov. 13, 1990

[54] QUINOLINE SUBSTITUTED OXOMETHYL OR THIOXOMETHYL GLYCINE DERIVATIVES AND ALDOSE REDUCTASE INHIBITION THEREWITH

[75] Inventors: Masao Murase, Nomuracho Kusatsu; Shigeaki Maruo, Minami-ai, both of Japan

[73] Assignee: Nippon Shinyaku Co., Ltd., Japan

[21] Appl. No.: 281,446

[22] Filed: Dec. 8, 1988

Related U.S. Application Data

[63] Continuation-in-part of Ser. No. 66,819, Jun. 5, 1987, abandoned.

[30] Foreign Application Priority Data

Jun. 27, 1986 [JP]  Japan ................................ 61-152149

[51] Int. Cl.$^5$ ................ C07D 215/50; C07D 215/22; A61K 31/77
[52] U.S. Cl. .................................. 514/311; 514/312; 546/156; 546/169
[58] Field of Search .................. 546/169, 156, 312; 514/311

[56] References Cited

U.S. PATENT DOCUMENTS

| | | | |
|---|---|---|---|
| 3,928,610 | 12/1975 | Weyer | 514/311 |
| 3,939,269 | 2/1976 | Aumuller | 514/311 |
| 4,195,984 | 4/1980 | Stein | 546/223 |
| 4,337,265 | 6/1982 | Treasurywala | 514/421 |

FOREIGN PATENT DOCUMENTS 52-16367  2/1977  Japan .

OTHER PUBLICATIONS

Budesinsky, A. (1960) Ceskoslov. Farm., 9, pp. 179–182, (Chem. Abstract 55:10435a).
Satoda, I. (1963) Yakugaku Zasshi, 83, pp. 93–98 (Chem. Abstract 59:3888g).
Poroshin, K. (1965) Dokl. Akad. Nauk Tadzh. SSR 8(1), pp. 21–23 (Chem. Abstract 63:16463g).
Halferich, B. (1966) J. Prakt. Chem., 33(1–2), pp. 39–49.
Dorland's Illustrated Medical Dictionary, 26th ed. (1982: W. B. Saunders Co.,; Philadelphia), pp. 368–369.
Chen. B. (1985) Yiyao Gongye, 16(2), pp. 66–68, (Chem. Abstract 102:87754r).
K. T. Poroshin et al., Chem. Abst. 61:7096f.
H. Meyer et al., Chem. Abst. 25:2999–3000.

*Primary Examiner*—David B. Springer
*Attorney, Agent, or Firm*—Jacobs & Jacobs

[57] ABSTRACT

A compound of the formula (I):

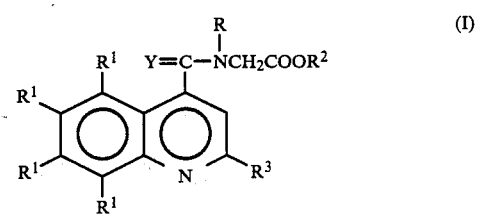

or a pharmaceutically acceptable salt thereof, wherein
Y is S or O;
R is hydrogen or alkyl having from about 1 to about 4 carbon atoms;
$R^1$ is hydrogen, alkyl having from about 1 to about 4 carbon atoms, alkoxy having from about 1 to about 4 carbon atoms, halogen or trifluoromethyl;
$R^2$ is hydrogen or unsubstituted or substituted alkyl having from about 1 to about 4 carbon atoms; and
$R^3$ is hydrogen, alkyl having from about 1 to about 6 carbon atoms, cycloalkyl having from about 3 to about 6 carbon atoms, alkoxy having from about 1 to about 4 carbon atoms, aryloxy having from about 6 to about 10 carbon atoms, alkylthio having from about 1 to about 4 carbon atoms, hydroxyalkoxy having from about 1 to about 4 carbon atoms, or unsubstituted or substituted phenyl is useful to obtain inhibition of aldose reduction in animals, including humans.

32 Claims, No Drawings

QUINOLINE SUBSTITUTED OXOMETHYL OR THIOXOMETHYL GLYCINE DERIVATIVES AND ALDOSE REDUCTASE INHIBITION THEREWITH

This application is a continuation-in-part of our copending application Ser. No. 066,819, filed Jun. 25, 1987, abandoned, which is incorporated herein by reference thereto.

The present invention relates to the use of glycine derivatives represented by the following general formula (I) and pharmaceutically acceptable salts thereof, which are aldose reductase inhibitors, in the treatment and/or prevention of diabetic complications:

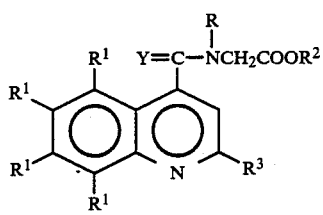

wherein
Y is S or O;
R is hydrogen or alkyl having from about 1 to about 4 carbon atoms;
$R^1$ is hydrogen, alkyl having from about 1 to about 4 carbon atoms, alkoxy having from about 1 to about 4 carbon atoms, halogen or trifluoromethyl;
$R^2$ is hydrogen or unsubstituted or substituted alkyl having from about 1 to about 4 carbon atoms; and
$R^3$ is hydrogen, alkyl having from about 1 to about 6 carbon atoms, cycloalkyl having from about 3 to about 6 carbon atoms, alkoxy having from about 1 to about 4 carbon atoms, aryloxy having from about 6 to about 10 carbon atoms, alkylthio having from about 1 to about 4 carbon atoms, hydroxyalkoxy having from about 1 to about 4 carbon atoms, or unsubstituted or substituted phenyl. The $R^1$ groups may be the same or different.

Neuropathy, retinal diseases and renal diseases are three of the main diabetic complications. Neuropathic sequelae are observed in about 50% of diabetic patients within 10 years after the onset of diabetes, while the other two are observed in about 80% of the patients within 20 years.

In the "polyol pathway", the enzyme aldose reductase, reduces an aldose (such as glucose, galactose, etc.) to the corresponding polyol (such as sorbitol, galactitol, etc.) which is then reduced to the simple sugar (fructose). Excessive sorbitol, galactitol, etc. produced by the aldose reductase enzyme accumulates in the crystalline lenses, peripheral nerves, kidneys, etc. of patients suffering from diabetes and galactosemia, whereupon the above described diabetic complications are caused. A number of aldose reductase inhibitors are at present undergoing clinical trials to prevent or reverse diabetic complications arising from intracellular accumulation of sorbitol caused by involvement of aldose reductase in the polyol pathway, such as sorbinol, M-79175, alconil, tolrestat, ICU-105552, Statil (ICI-128436) and epalrestat (ONO-2235). Such aldose reductase implicated diabetic complications include cataract, retinopathy, microangiopathy, nephropathy, thickening of retinal basement membranes, renal hypertrophy, neuropathy, autonomic neuropathy, peripheral neuropathy and the like. See, e.g. Beyer-Mears et al, Diabetes, 33, 604–607 (Jun., 1984); Beyer-Mears et al, Diabetes, 34, 15–21 (Jan., 1985); Kador et al, Annu. Rev. Pharmacol. Toxicol., 25, 691–714 (1985); Kador et al, J. Med. Chem., 28, No. 7, 841–849 (1985); Pfeifer, Am. J. Med., 79, No. 5A, 18–23 (1985); Jaspan et al, Am. J. Med., 79, No. 5A, 24–37 (1985); Cameron et al, Diabetologia, 29, 168–174 (1986); Robinson et al, Diabetes, 35, 295–299 (1986); Jaspan et al, Metab. Clin. Exp., 35, No. 4, Suppl. 1, 83–92 (1986); Benfield, Drugs, 32, Suppl. 2, 43–55 (1986); Raskin et al J. Med., 83, No. 2., 298–306 (1987); Polyol Pathway And Its Role In Diabetic Complications, Sakamoto et al, Elseiver Science Publishers BV (Biomedical Division), 1988, pages 496–501 and 541–544; and Burg et al, J. Clin. Invest., 81, No. 3, 635–640 (1988).

As used in this specification and the appended claims, the term "diabetic complications" means diabetic complications involving the aldose reductase enzyme.

Compounds (I) of the present invention are aldose reductase inhibitors having excellent pharmacological action with low toxicity.

The compound [(2-phenylquinolin-4-yl)carbonyl]glycine (C.A. 59=3889) is known. However, this compound was synthesized as an antipyretic and analgesic drug and it does not exhibit the aldose reductase inhibiting action of the compounds of the present invention.

The accompanying Examples illustrate representative compounds (I) of the invention. Suitably, the groups R, $R^1$, $R^2$ and $R^3$ may be as exemplified below. Presently preferred compounds (I) of the invention include the following and their pharmaceutically acceptable salts:

beta-hydroxyethyl ester of N-[(2-phenylquinolin-4-yl)-thioxomethyl]-N-methylglycine;

beta-hydroxyethyl ester of N-[(2-methyl-8-trifluoromethylquinolin-4-yl)-thioxomethyl]-N-methylglycine;

beta-hydroxyethyl ester of N-[{2-(2-fluorophenyl)-7-fluoroquinolin-4-yl}-thioxomethyl]-N-methylglycine;

beta-hydroxyethyl ester of N-[2-ethyl-8-trifluoromethylquinolin-4-yl)thioxomethyl]-N-methyl glycine;

N-[2-phenyl-6-chloroquinolin-4-yl)-thioxomethyl]-N-methylglycine; and

N-{[2-(4-methylphenyl)-6-fluoroquinolin-4-yl]thioxomethyl}-N-methylglycine.

Examples of alkyl having from about 1 to about 4 carbon atoms include straight or branched chain alkyl, such as methyl, ethyl, n-propyl, isopropyl, n-butyl, isobutyl, and the like.

Examples of alkoxy having from about 1 to about 4 carbon atoms include straight or branched chain alkoxy, such as methoxy, ethoxy, n-propoxy, isopropoxy, n-butoxy, isobutoxy, sec-butoxy, tert-butoxy, etc.

Examples of halogen include chlorine, bromine, iodine, fluorine, etc.

When $R^2$ is substituted alkyl, the substituents may be hydroxyl, alkoxy, hydroxyalkoxy, acyloxy, amino, alkylamino, dialkylamino, etc., the alkoxy, hydroxyalkoxy and acyloxy and the alkyl moiety of alkyl- and dialkylamino each having from about 1 to about 4 carbon atoms. Examples of acyloxy include acetoxy, propionyloxy, n-butyryloxy, etc.

Examples of alkyl having from about 1 to about 6 carbon atoms include straight or branched chain alkyl, such as, for example, methyl, ethyl, n-propyl, isopropyl, n-butyl, isobutyl, sec-butyl, tert-butyl, n-pentyl, isopentyl, n-hexyl, isohexyl, etc.

Examples of cycloalkyl having from about 3 to about 6 carbon atoms include cyclopropyl, cyclobutyl, cyclopentyl, cyclohexyl, etc. Examples of aryloxy having from about 6 to about 10 carbon atoms include phenoxy, naphthyloxy, etc.

Suitable alkylthio having from about 1 to about 4 carbon atoms includes straight or branched chain alkylthio, such as methylthio, ethylthio, n-propylthio, isopropylthio, n-butylthio, isobutylthio, etc.

Examples of hydroxyalkoxy having from about 1 to about 4 carbon atoms include hydroxymethoxy, hydroxyethoxy, hydroxypropoxy, hydroxybutoxy, etc.

When $R^3$ is substituted phenyl, there may be from 1 to 3 substituents, which may be the same or different. Examples of such substituents include alkyl having from about 1 to about 8 carbon atoms, cycloalkyl having from about 3 to about 6 carbon atoms, alkoxy having from about 1 to about 4 carbon atoms, halogen and trifluoromethyl.

Suitable pharmaceutically acceptable salts of (I) include salts with mineral acids (such as hydrochloric acid, sulphuric acid, nitric acid, phosphoric acid, hydrofluoric acid, hydrobromic acid, etc.), salts with organic acids (such as formic acid, acetic acid, tartaric acid, lactic acid, citric acid, fumaric acid, maleic acid, succinic acid, methanesulphonic acid, ethanesulphonic acid, benzenesulphonic acid, toluenesulphonic acid, naphthalenesulphonic acid, camphorsulphonic acid, etc.) and salts with an alkali metal or an alkaline earth metal (such as sodium, potassium, calcium, etc.).

The compounds (I) of the present invention may be manufactured by the following routes:

an acid anhydride, acid halide (acid chloride, acid bromide, etc.), activated ester (e.g., imidazolide, 1-benzotriazole, 2,4,5-trichlorophenyl, succinimide, etc.) or a mixed acid anhydride (e.g. anhydride with methyl carbonate; anhydride with ethyl carbonate; anhydride with isobutyl carbonate; etc.).

For example, the activated ester of (III) may be prepared by reacting (III), usually in an inert solvent (e.g. a halogenated hydrocarbon type solvent such as methylene chloride, chloroform, etc.; an ether type solvent such as tetrahydrofuran, dioxane, etc.; or an aprotic solvent such as acetonitrile, N,N-dimethylformamide, etc.) with 1-hydroxybenzotriazole or the like and a condensation agent (e.g. N,N'-dicyclohexylcarbodiimide) to convert (III) to the activated ester of (III), which is then condensed with (IV) at $-10°$ C. to room temperature to give (Ia).

The amount of compound (IV) is preferably 1.2 to 2.5 moles per mole of (III).

The amide ester (Ia) is then reacted, in an inert solvent (e.g. xylene, toluene, etc.), with phosphorus pentasulfide or Lawesson's reagent under anhydrous condition to give (Ib). Preferably, the reaction is conducted in the presence of an organic base, such as N-ethylmorpholine, triethylamine, pyridine, etc.

The reaction temperature is preferably from 80° to 150° C. and, to be more convenient, at the boiling point of the solvent used.

The amount of the phosphorus pentasulfide is preferably 1.1 to 3 moles per mole of (Ia). The amount of Lawesson's reagent is preferably 0.5 to 2 moles per mole of (Ia).

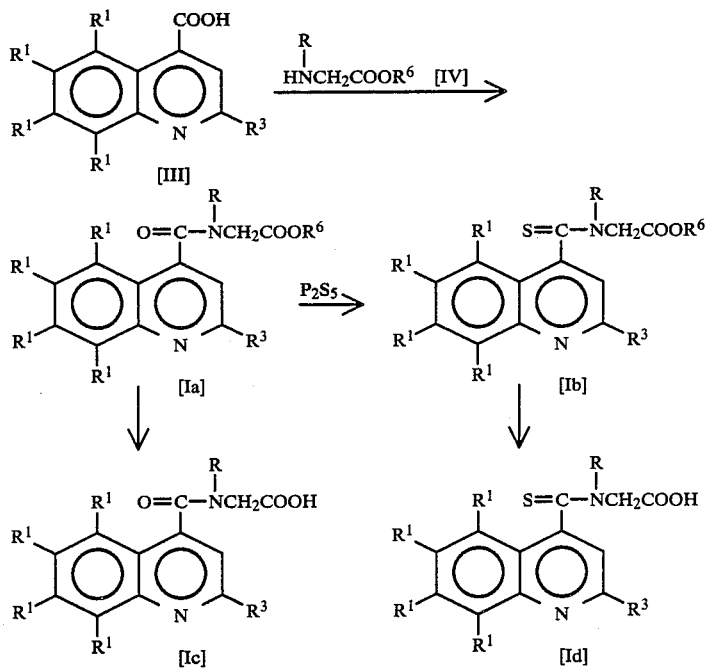

($R$, $R^1$ and $R^3$ are as previously defined; and $R^6$ is alkyl of 1 to 4 carbon atoms, unsubstituted or substituted as defined for $R^2$.)

Each step will be illustrated in more detail as follows.

Compound (III) or a reactive derivative thereof is reacted with (IV) to give (Ia). This reaction can be carried out by analogy to methods known per se. Suitable reactive derivatives of (III) include, for example, If desired, (Ib) may be hydrolyzed to give (Id). This hydrolysis reaction can be easily conducted in water, alcohol (e.g. methanol, ethanol, etc.) or a mixture thereof using an alkali, such as sodium hydroxide or potassium hydroxide. The reaction is usually conducted at 20° to 100° C. The amount of the alkali used is usually 1 to 5 moles per mole of (Ib). This hydrolysis reaction may be similarly carried out using a mineral acid, such as hydrochloric acid, sulphuric acid, phosphoric acid, etc.

If desired, (Ia) may be hydrolyzed to give (Ic). This hydrolysis reaction may be conducted using the same reaction conditions as mentioned hereinabove.

When a compound having hydroxy group(s), such as the hydroxyalkyl ester of glycine or N-alkylglycine is used in the above method, the hydroxy group(s) may be protected, subjected to reaction with (III), and the protective group(s) is/are removed therefrom to give the desired compound.

Any suitable protective group that can be easily removed can be used, such as those usually used for the protection of hydroxy groups including methyl, trimethylsilyl, tert-butyldimethylsilyl, acetyl, tetrahydropyranyl, methylthiomethyl, methoxymethyl, beta-methoxyethoxymethyl, benzyl, etc.

When the compound (Ia) or (Ib) is an ester (i.e. $R^6$ is alkyl), it may be subjected to a transesterification reaction by a method known per se with an alcohol corresponding to the desired ester (I). Thus, the ester (Ia) or (Ib) is reacted with 10 to 100 moles of the alcohol per mole of the ester in the presence or absence of a suitable inert solvent (e.g. benzene, toluene, etc.) in the presence of a catalytic amount of an alkali (e.g. sodium hydride, sodium hydroxide, potassium hydroxide, potassium carbonate, sodium carbonate, sodium bicarbonate, etc.) in vacuo (20 to 30 mmHg) at 50° to 100° C. (preferably at 60° to 80° C.) to give the desired ester compound (I). It is preferred to use a basic catalyst (e.g. potassium alkoxide, sodium alkoxide, etc.) and, when $R^6$ is methyl, a molecular sieve A is preferably present so that the resulting methanol is selectively adsorbed therein or the reaction is conducted in vacuo (20 to 30 mmHg) to afford the desired ester compound (I) in high yield. Another preferred embodiment uses an acidic catalyst (e.g. sulphuric acid, p-toluenesulphonic acid, etc.) and an alcohol corresponding to the desired ester in a large excess or, when $R^1$ is methyl, the low-boiling methanol is removed therefrom to afford the desired ester compound (I) in high yield.

The carboxylic acids (Ic) and (Id) (i.e. $R^2$ is hydrogen), may be, if desired, esterified to an ester (I) (i.e. $R^2$ is alkyl). This esterifying reaction may be conducted by methods known per se, such as the use of thionyl chloride with an alcohol, concentrated sulphuric acid with an alcohol, an alcohol with a condensation agent, or alkyl halide with an alcoholate.

Some compounds (III) are new and they may be manufactured either by analogy to known methods (cf. The Chemistry of Heterocyclic Compounds, 32(1), 197, 125; Chemische Berichte, 41, 3884, 1908) or by a method which is the same or similar to that given in the Reference Examples below.

Compound (IV) may be manufactured by known methods.

The resulting compound (I) can be separated/purified by known methods per se, such as, for example, concentration, liquid phase conversion, transferring to another solvent, extraction with solvent, crystallization, recrystallization, fractional distillation, chromatography, etc.

The compounds (I) of the invention are used in the treatment and/or prevention of diabetic complications. In particular, compounds (I) are used to obtain an aldose reductase inhibition effect in animals, including humans, by administering to an animal in need thereof an amount of the compound (I) of the invention effective to inhibit aldose reductase in said animal. Preferably, compound (I) will be administered in the form of a pharmaceutical composition, comprising an effective amount of the compound (I) in combination with a pharmaceutically acceptable, nontoxic, inert diluent or carrier, the carrier comprising one or more solid, semi-solid or liquid diluents, fillers and formulation adjuvants which are nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses, or, alternatively, one half, third or fourth of a single dose. A single dose preferably contains an amount sufficient to produce the desired aldose reductase inhibition effect upon administration at one application of one or more dosage units according to predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dosage for humans will be from about 1 to about 1000 mg, preferably from about 100 to about 500 mg. In some instances, a sufficient therapeutic effect can be obtained at a lower dose, while in others a large dose will be required.

While the routes of administration of the compound (I) of the invention include oral, parenteral (e.g., intramuscular, intraperitoneal and intravenous), topical and rectal, oral administration is particularly preferred.

The preferred pharmaceutical compositions are therefore those in a form suitable for oral administration, such as tablets, capsules and liquids.

The following Examples are provided for further illustration of the present invention. However, the Examples are not intended the limit the present invention.

REFERENCE EXAMPLE 1

8-Trifluoromethylquinoline-4-carboxylic acid

Pyruvic acid (7.2 g) was dropped into 67 ml of ice-cooled 33% aqueous solution of potassium hydroxide containing 10.0 g of 7-trifluoromethylisatin and the mixture was stirred for about 20 hours and then heated to reflux for 30 minutes. This was cooled, strongly acidified with concentrated hydrochloric acid, the crystals separated out therefrom were collected by filtration, washed with water, dissolved in methanol, and treated with an activated charcoal to give 5.6 g of colourless crystals of 8-trifluoromethyl-2,4-quinolinedicarboxylic acid.

This was heated in diphenyl ether at 215° to 220° C. (bath temperature) and stirred for 40 minutes. This was then cooled, the crystals separated out therefrom were collected by filtration, ethyl acetate was added to the filtrate, and the mixture was extracted with diluted aqueous solution of sodium hydroxide. The aqueous extract was acidified with 10% hydrochloric acid, extracted with ethyl acetate, the extract was washed with water and dried, and the solvent was evaporated therefrom to give crude crystals.

They were combined with the previously-obtained crystals, treated with activated charcoal, the solvent was evaporated therefrom, and the resulting crystals were washed with isopropyl ether to give 3.3 g of 8-trifluoromethyl-4-quinolinecarboxylic acid.

REFERENCE EXAMPLE 2

2-Methoxyquinoline-4-carboxylic acid

Thionyl chloride (70 ml) and one drop of N,N-dimethylformamide were added to 3.25 g of 4-methoxycarbonyl-2-quinolone and the mixture was heated to reflux for 4 hours. After the reaction was completed, thionyl chloride was evaporated therefrom in vacuo, then toluene was added thereto, and the solvent was evaporated in vacuo. The residue was not purified but dissolved in small amount of methanol, the solution was added to 100 ml of methanolic solution of sodium methoxide (prepared from 0.44 g of sodium), and the mixture was heated to reflux for 5 hours. Methanol was evaporate therefrom in vacuo, water was added to the residue, the mixture was extracted with ethyl acetate, the extract was washed with water and dried, and ethyl acetate was evaporated therefrom to give 3.15 g of colourless crystals of methyl 2-methoxyquinoline-4-carboxylate.

The resulting compound (1.82 g) was dissolved in 60 ml of methanol, 9 ml of 2N aqueous solution of sodium hydroxide was added thereto, the mixture was stirred for 2 hours at room temperature, methanol was evaporated therefrom in vacuo, the residue was dissolved in 100 ml of water, the solution was washed with ether, adjusted to pH 4 with 10% hydrochloric acid, the crystals separated out therefrom were collected by filtration, washed with water, dried in vacuo, and 2-methoxyquinoline-4-carboxylic acid in colourless crystals was prepared in 86% yield. M.p. 185°–186° C.

EXAMPLE 1

Methyl ester of N-[(2-phenylquinolin-4-yl)carbonyl]-N-methylglycine

2-Phenylquinoline-4-carboxylic acid (5 g), 4.9 g of dicyclohexylcarbodiimide and 4 g of 1-hydroxybenzotriazole were dissolved in 150 ml of anhydrous N,N-dimethylformamide and the mixture was stirred at room temperature for 1 hour. Then a solution of 5.6 g of N-methylglycine methyl ester hydrochloride and 7 ml of N-methylmorpholine in 50 ml of anhydrous N,N-dimethylformamide was added to the above reaction solution. The mixture was stirred at room temperature for 12 hours. The reaction solution was then poured over into 300 ml of water, the mixture was extracted with ethyl acetate, the ethyl acetate layer was washed with water, dried with magnesium sulfate, the solvent was evaporated in vacuo, and the residue was collected by filtration using isopropyl ether followed by washing to give 4.6 g of white crystals, m.p. 98°–104° C.

EXAMPLE 2

Methyl ester of N-[(2-phenylquinolin-4-yl)thioxomethyl]-N-methylglycine

The compound (4.6 g) obtained in the above and 3.1 g of Lawesson's reagent were dissolved in 100 ml of toluene and the mixture was heated to reflux for 1.5 hours with stirring. After the reaction, toluene was removed in vacuo and the residue was purified by subjecting to a silica gel column chromatography (silica gel Wako C-200 and chloroform) to give 2.6 g of pale yellow crystals, m.p. 133°–136° C.

Elem. Anal. $C_{20}H_{18}N_2O_2S$. Calcd (%) C 68.55, H 5.18, N 7.99. Found (%) C 68.67, H 5.26, N 7.85.

EXAMPLE 3

N-[(2-Phenylquinolin-4-yl)thioxomethyl]-N-methylglycine

The methyl ester (2.6 g) obtained in the above was dissolved in 50 ml of methanol, 7.7 ml of 2N sodium hydroxide was added, and the mixture was stirred at room temperature for 2 hours. After the reaction, the reaction solution was adjusted to pH 4–5 with 10% hydrochloric acid, methanol was evaporated therefrom, the residue was extracted with ethyl acetate, the extract was washed with water, dried with magnesium sulfate, the solvent was evaporated therefrom, the residue was purified by a column chromatography (silica gel and chloroform), and the resulting oil was crystallized by a mixed solvent of isopropyl ether and methanol followed by filtering, washing and drying to give 1.4 g of yellow crystals, m.p. 228°–230° C.

Elem. Anal. $C_{19}H_{16}N_2O_2S$: Calcd (%) C 67.84, H 4.79, N 8.33. Found (%) C 67.75, H 5.04, N 8.12.

EXAMPLE 4

β-Hydroxyethyl ester of N-[(2-phenylquinolin-4-yl)thioxomethyl]-N-methylglycine To 1.2 g of the carboxylic acid obtained in the above Example 3 were added 60 ml of ethyleneglycol and 1.5 ml of concentrated sulfuric acid and the mixture was heated with stirring at 80° C. for 2 hours. After the reaction, it was poured into water, the mixture was extracted with ethyl acetate, the extract was washed with water, dried with magnesium sulfate, the solvent was evaporated therefrom, and the residue was crystallized from isopropyl ether followed by washing to give 0.99 g of pale yellow crystals, m.p. 114°–115° C. Hydrochloride, m.p. 128° C. (decompn.)

Elementary analysis calculated as $C_{21}H_{20}N_2O_3S$: Calcd (%): C 66.30, H 5.30, N 7.36. Found (%): C 66.29, H 5.34, N 7.34.

EXAMPLE 5

β-Hydroxyethyl ester of N-[(2-phenylquinolin-4-yl)thioxomethyl]-N-methylglycine To 80 ml of ethyleneglycol was added 230 mg of sodium hydride (60% dispersion in mineral oil) and, with stirring at room temperature, a mixture of 10 g of the methyl ester (obtained in the Example 2) and 15 ml of toluene was added thereto, the mixture was stirred on an oil bath at 80° C. for 2 hours, cooled, poured over into a mixture of ice water and 15 ml of 10% hydrochloric acid, the resulting mixture was extracted with 200 ml of ethyl acetate twice, the combined extracts were washed with saturated sodium bicarbonate solution, washed with water, dried, ethyl acetate was evaporated therefrom, and the residue was crystallized from isopropyl ether to give 7.0 g of pale yellow crystals, m.p. 114°–115° C.

Elem. Anal. $C_{21}H_{20}N_2O_3S$: Calcd (%) C 66.30, H 5.30, N 7.36. Found (%) C 66.44, H 5.47, N 7.28.

EXAMPLE 6 beta-Hydroxyethyl ester of N-[(2-methyl-8-trifluoromethylquinolin-4-yl)thioxomethyl]-N-methylglycine Methyl ester (14, 9 g) of N-[(2-methyl-8-trifluoromethylquinolin-4-yl)thioxomethyl]-N-methylglycine was added to 60 ml of ethyleneglycol. The mixture was stirred, and 0.4 g of 60% sodium hydride was gradually added thereto. The mixture was stirred at 80° C. for 30 minutes and, with removal of methanol produced thereby in vacuo, it was stirred at the same temperature for 1 hour more. After being cooled, the mixture was poured over into ice water, extracted with ethyl acetate, the extract was washed with water, and dried and concentrated, the residue was purified by subjecting to a column chromatography (silica/chloroform), and crystallised/washed from/with isopropyl ether to give 14.22 g of pale yellow powder. M.p. 99°-101° C.

Elem. Anal. $C_{17}H_{17}F_3N_2O_3S$: Calcd (%): C 52.84, H 4.43, N 7.25. Found (%): C 53.14, H 4.62, N 7.18.

Similarly was prepared the following compounds:

β-Hydroxyethyl ester of N-[{2-(2-fluorophenyl)-7-fluoroquinolin-4-yl}thioxomethyl]-N-methylglycine. M.p. 147°-148° C. (decompn.)

Elementary analysis for $C_{21}H_{18}N_2O_3S$: Calcd (%): C 60.57, H 4.36, N 6.73. Found (%): C 60.61, H 4.54, N 6.65.

β-Hydroxyethyl ester of N-[(2-ethyl-8-trifluoromethylquinolin-4-yl)thioxomethyl]-N-methylglycine. M.p. 98°-101° C.

Elem. Anal. $C_{18}H_{19}F_3N_2O_3S$: Calcd (%) C: 53.99 H: 4.78 N: 7.00. Found (%) C: 54.25 H: 4.74 N: 7.00.

β-Hydroxyethyl ester of N-[(2,6-dimethylquinolin-4-yl)-thioxomethyl]-N-methylglycine. M.p. 167°-170° C.

Elem. Anal. $C_{17}H_{20}N_2O_3S$: Calcd (%) C: 61.42 H: 6.06 N: 8.43. Found (%) C: 61.50 H: 6.16 N: 8.10.

β-Hydroxyethyl ester of N-[(2-methyl-6-chloroquinolin-4-yl)thioxomethyl]-N-methylglycine. M.p. 193°-195° C.

Elem. Anal. $C_{16}H_{17}ClN_2O_3S$: Calcd (%) C: 54.47 H: 4.86 N: 7.94. Found (%) C: 54.29 H: 5.01 N: 7.67.

β-Hydroxyethyl ester of N-[(2-methylthioquinolin-4-yl)thioxomethyl]-N-methylglycine. M.p. 139°-140° C.

Elem. Anal. $C_{16}H_{18}N_2O_3S_2$: Calcd (%) C: 54.84 H: 5.18 N: 7.99. Found (%) C: 54.87 H: 5.08 N: 7.90.

β-Hydroxyethyl ester of N-[{6,8-dichloro-2-(4-methylphenyl)quinolin-4-yl}thioxomethyl]-N-methylglycine. M.p. 177°-180° C.

Elem. Anal. $C_{22}H_{20}Cl_2N_2O_3S$: Calcd (%) C: 57.35 H: 4.35 N: 6.05. Found (%) C: 57.17 H: 4.24 N: 6.36.

β-Hydroxyethyl ester of N-[(6,8-dichloro-2-phenylquinolin-4-yl)-thioxomethyl]-N-methylglycine. M.p. 163°-167° C.

Elem. Anal. $C_{21}H_{18}Cl_2N_2O_3S$: Calcd (%) C: 56.13 H: 4.04 N: 6.23. Found (%) C: 55.91 H: 4.18 N: 6.14.

β-Hydroxyethyl ester of N-[{2-(2-fluorophenyl)-quinolin-4-yl}thioxomethyl]-N-methylglycine. M.p. 105°-107° C.

Elem. Anal. $C_{21}H_{19}F N_2O_3S$: Calcd (%) C: 63.30 H: 4.81 N: 7.03. Found (%) C: 63.28 H: 4.78 N: 7.18.

β-Hydroxyethyl ester of N-[(7-fluoro-2-methylquinolin-4-yl)thioxomethyl]-N-methylglycine. M.p. 108°-111° C.

Elem. Anal. $C_{16}H_{17}F N_2O_3S$: Calcd (%) C: 57.13 H: 5.09 N: 8.33. Found (%) C: 57.29 H: 5.07 N: 8.39.

β-Hydroxyethyl ester of N-[(quinolin-4-yl)thioxomethyl]-N-methylglycine. M.p. 127°-131° C.

Elem. Anal. $C_{15}H_{16}N_2O_3S$: Calcd (%) C: 59.19 H: 5.30 N: 9.20. Found (%) C: 59.28 H: 5.31 N: 9.16.

N-{[2-(3-Methoxyphenyl)quinolin-4-yl]thioxomethyl}glycine. M.p. 208°-209° C. (decompn).

Elem. Anal. $C_{19}H_{16}N_2O_3S$: Calcd (%) C: 64.76 H: 4.58 N: 7.95. Found (%) C: 64.59 H: 4.70 N: 7.98.

N-{[2-(2-Methoxyphenyl)-6-bromoquinolin-4-yl]thioxomethyl}-N-methylglycine. M.p. 239°-241° C. (decompn.).

Elem. Anal. $C_{20}H_{17}BrN_2O_3S$: Calcd (%) C: 53.94 H: 3.85 N: 6.29. Found (%) C: 53.70 H: 3.88 N: 6.25.

N-{[2-(2-Chlorophenyl)-6-methylquinolin-4-yl]thioxomethyl}-N-methylglycine. M.p. 224°-226° C. (decompn).

Elem. Anal. $C_{20}H_{17}ClN_2O_2S$: Calcd (%) C: 62.41 H: 4.45 N: 7.28. Found (%) C: 62.47 H: 4.46 N: 7.11.

N-{[2-(4-Chlorophenyl)quinoline-4-yl]carbonyl}-N-methylglycine. M.p. 181°-183° C.

Elem. Anal. $C_{19}H_{15}ClN_2O_3$: Calcd (%) C: 64.32 H: 4.26 N: 7.90. Found (%) C: 64.33 H: 4.26 N: 7.84.

N-{[2-(4-Chlorophenyl)quinoline-4-yl]thioxomethyl}-N-methylglycine. M.p. 228°-229° C.

Elem. Anal. $C_{19}H_{15}ClN_2O_2S$: Calcd (%) C: 61.54 H: 4.08 N: 7.55. Found (%) C: 61.74 H: 3.92 N: 7.52.

N-{[2-(4-Methoxyphenyl)quinolin-4-yl]carbonyl}-N-methylglycine. M.p. 194°-198° C.

Elem. Anal. $C_{20}H_{18}N_2O_4$: Calcd (%): C: 68.56 H: 5.18 N: 7.80. Found (%): C: 68.45 H: 5.60 N: 8.16.

N-{[2-(4-Methoxyphenyl)quinoline-4-yl]thioxomethyl}-N-methylglycine. M.p. 240° C. (decompn).

Elem. Anal. $C_{20}H_{18}N_2O_3S$: Calcd (%): C: 65.56 H: 4.95 N: 7.64. Found (%): C: 65.34 H: 4.98 N: 7.55.

N-{[2-(4-Methylphenyl)quinolin-4-yl]thioxomethyl}-N-methylglycine. M.p. 195° C. (decompn).

Elem. Anal. $C_{20}H_{18}N_2O_2S.\frac{1}{2}H_2O$: Calcd (%): C: 66.83 H: 5.33 N: 7.79. Found (%): C: 67.04 H: 5.25 N: 7.58.

N-{[2-(4-Chlorophenyl)-6-methylquinolin-4-yl]thioxomethyl}-N-methylglycine. M.p. 258°-260° C.

Elem. Anal. $C_{20}H_{17}ClN_2O_2S$: Calcd (%): C: 62.41 H: 4.45 N: 7.28. Found (%): C: 62.17 H: 4.39 N: 7.28.

N-{[6-Chloro-2-(4-methoxyphenyl)quinolin-4-yl]thioxomethyl}-N-methylglycine. M.p. 240°-242° C.

Elem. Anal. $C_{20}H_{17}ClN_2O_3S$: Calcd (%): C: 59.92 H: 4.27 N: 6.99. Found (%): C: 59.65 H: 4.21 N: 6.88.

N-{[6,8-Dichloro-2-(4-methylphenyl)quinolin-4-yl]thioxomethyl}-N-methylglycine. M.p. 229°-230° C. (decompn).

Elem. Anal. $C_{20}H_{16}Cl_2N_2O_2S$: Calcd (%): C: 57.29 H: 3.85 N: 6.68. Found (%): C: 57.33 H: 4.01 N: 6.56.

N-{[2-(2,5-Dimethoxyphenyl)quinolin-4-yl]thioxomethyl}-N-methylglycine. M.p. 140° C. (decompn).

Elem. Anal. $C_{21}H_{20}N_2O_4S$: Calcd (%): C: 63.62 H: 5.08 N: 7.07. Found (%): C: 63.31 H: 5.23 N: 6.71.

N-{[2-(2,4-Dichlorophenyl)-6-methylquinolin-4-yl]thioxomethyl}-N-methylglycine. M.p. 223°-229° C. (decompn.).

Elem. Anal. $C_{20}H_{16}Cl_2N_2O_2S$: Calcd (%): C: 57.29 H: 3.85 N: 6.68. Found (%): C: 57.20 H: 4.07 N: 6.54.

N-{[2-(3-Methoxyphenyl)quinolin-4-yl]thioxomethyl}-N-methylglycine. M.p. 139°-141° C.

Elem. Anal. $C_{20}H_{18}N_2O_3S.\frac{3}{8}H_2O$: Calcd (%): C: 63.47 H: 5.15 N: 7.40. Found (%): C: 63.37 H: 5.47 N: 6.99.

N-{[2-(3-Chlorophenyl)-6-methylquinolin-4-yl]thioxomethyl}-N-methylglycine. M.p. 223°-225° C.

Elem. Anal. C$_{20}$H$_{17}$ClN$_2$O$_2$S: Calcd (%): C: 62.41 H: 4.45 N: 7.28. Found (%): C: 62.22 H: 4.51 N: 7.17.

N-{[2-(2-Methoxyphenyl)quinolin-4-yl]thioxomethyl}-N-methylglycine. M.p. 155°–160° C. (decompn).

Elem. Anal. C$_{20}$H$_{18}$N$_2$O$_3$S: Calcd (%): C: 65.56 H: 4.95 N: 7.64. Found (%): C: 65.34 H: 4.98 N: 7.67.

N-{[2-(2-Chlorophenyl)-6-methylquinolin-4-yl]thioxomethyl}-N-methylglycine. M.p. 224°–226° C. (decompn.).

Elem. Anal. C$_{20}$H$_{17}$ClN$_2$O$_2$S: Calcd (%): C: 62.41 H: 4.45 N: 7.28. Found (%): C: 62.47 H: 4.46 N: 7.11.

N-[(2-Phenyl-6-methylquinolin-4-yl)thioxomethyl]-N-methylglycine. M.p. 253°–255° C. (decompn.).

Elem. Anal. C$_{20}$H$_{18}$N$_2$O$_2$S: Calcd (%): C: 68.55 H: 5.18 N: 8.00. Found (%): C: 68.42 H: 5.35 N: 7.90.

N-{[2-(3-Methoxyphenyl)-6-chloroquinolin-4-yl]thioxomethyl}-N-methylglycine. M.p. 134°–137° C.

Elem. Anal. C$_{20}$H$_{17}$ClN$_2$O$_3$S.3/5H$_2$O: Calcd (%): C: 58.35 H: 4.46 N: 6.80. Found (%): C: 58.24 H: 4.48 N: 6.62.

N-{[2-(3-Methoxyphenyl)-6-methylquinolin-4-yl]thioxomethyl}-N-methylglycine. M.p. 143° C. (decompn.).

Elem. Anal. C$_{21}$H$_{20}$N$_2$O$_3$S.½H$_2$O: Calcd (%): C: 64.76 H: 5.43 N: 7.19. Found (%): C: 64.84 H: 5.77 N: 6.97.

N-{[2-(2-Fluorophenyl)-6-methylquinolin-4-yl]thioxomethyl}-N-methylglycine. M.p. 266° C.

Elem. Anal. C$_{20}$H$_{17}$FN$_2$O$_2$S: Calcd (%): C: 65.20 H: 4.65 N: 7.60. Found (%): C: 64.89 H: 4.68 N: 7.47.

N-{[2-(2-Methylphenyl)-6-methylquinolin-4-yl]thioxomethyl}-N-methylglycine. M.p. 140° C. (decompn).

Elem. Anal. C$_{21}$H$_{20}$N$_2$O$_2$S: Calcd (%): C: 69.21 H: 5.53 N: 7.69. Found (%): C: 68.91 H: 5.81 N: 7.32.

N-{[2-(2-Chlorophenyl)-8-trifluoromethylquinolin-4-yl]thioxomethyl}-N-methylglycine. M.p. 199°–201° C.

Elem. Anal. C$_{20}$H$_{14}$ClF$_3$N$_2$O$_2$S: Calcd (%): C: 54.74 H: 3.22 N: 6.38. Found (%): C: 54.79 H: 3.33 N: 6.31.

N-{[2-(2-Trifluoromethylphenyl)-6-methylquinolin-4-yl]thioxomethyl}-N-methylglycine. M.p. 218°–222° C.

Elem. Anal. C$_{21}$H$_{17}$F$_3$N$_2$O$_2$S: Calcd (%): C: 60.28 H: 4.01 N: 6.69. Found (%): C: 60.41 H: 4.27 N: 6.64.

N-{[2-(3-Methoxyphenyl)-7-fluoroquinolin-4-yl]thioxomethyl}-N-methylglycine. M.p. 128°–140° C. (decompn).

Elem. Anal. C$_{20}$H$_{17}$FN$_2$O$_3$S: Calcd (%): C: 62.49 H: 4.46 N: 7.29. Found (%): C: 62.48 H: 4.77 N: 6.94.

N-{[2-(3-Methoxyphenyl)-8-trifluoromethylquinolin-4-yl]thioxomethyl}-N-methylglycine. M.p. 154°–155° C. (decompn).

Elem. Anal. C$_{21}$H$_{17}$FN$_2$O$_3$S.2H$_2$O: Calcd (%): C: 53.61 H: 4.50 N: 5.95. Found (%): C: 53.62 H: 4.00 N: 5.85.

N-{[2-(2-Methoxyphenyl)-6-methylquinolin-4-yl]thioxomethyl}-N-methylglycine. M.p. 155° C. (decompn).

Elem. Anal. C$_{21}$H$_{20}$N$_2$O$_3$S: Calcd (%): C: 66.30 H: 5.30 N: 7.36. Found (%): C: 66.06 H: 5.58 N: 7.09.

N-{[2-(2-Methylphenyl)quinolin-4-yl]thioxomethyl}-N-methylglycine. M.p. 140° C. (decompn).

Elem. Anal. C$_{20}$H$_{18}$N$_2$O$_2$S.3/2H$_2$O: Calcd (%): C: 63.64 H: 5.61 N: 7.42. Found (%): C: 63.70 H: 5.33 N: 7.35.

N-{[2-(2,3,4-Trimethoxyphenyl)-6-methylquinolin-4-yl]thioxomethyl}-N-methylglycine. M.p. 145° C. (decompn).

Elem. Anal. C$_{23}$H$_{24}$N$_2$O$_5$S.½H$_2$O: Calcd (%): C: 61.46 H: 5.61 N: 6.23. Found (%): C: 61.27 H: 5.70 N: 5.84.

N-{[2-(2-Trifluoromethylphenyl)quinolin-4-yl]thioxomethyl}-N-methylglycine. M.p. 140°–150° C. (decompn).

Elem. Anal. C$_{20}$H$_{15}$F$_3$N$_2$O$_2$S.½H$_2$O: Calcd (%): C: 58.11 H: 3.90 N: 6.78. Found (%): C: 58.31 H: 3.82 N: 6.76.

N-{[2-(2-Fluorophenyl)quinolin-4-yl]thioxomethyl}-N-methylglycine. M.p. 198°–201° C. (decompn).

Elem. Anal. C$_{19}$H$_{15}$FN$_2$O$_2$S: Calcd (%): C: 64.39 H: 4.27 N: 7.90. Found (%): C: 64.57 H: 4.37 N: 7.83.

N-[(2-Phenyl-8-trifluoromethylquinolin-4-yl)thioxomethyl]-N-methylglycine. M.p. 208°–209° C.

Elem. Anal. C$_{20}$H$_{15}$F$_3$N$_2$O$_2$S: Calcd (%): C: 59.40 H: 3.74 N: 6.93. Found (%): C: 59.19 H: 3.73 N: 6.73.

N-[(2-Phenyl-6-chloroquinolin-4-yl)thioxomethyl]-N-methylglycine. M.p. 259°–260° C. (decompn.).

Elem. Anal. C$_{19}$H$_{15}$ClN$_2$O$_2$S: Calcd (%): C: 61.54 H: 4.08 N: 7.55. Found (%): C: 61.19 H: 4.08 N: 7.52.

N-{[2-(3-Chlorophenyl)quinolin-4-yl]thioxomethyl}-N-methylglycine. M.p. 136°–140° C. (decompn.).

Elem. Anal. C$_{19}$H$_{15}$ClN$_2$O$_2$S: Calcd (%): C: 61.54 H: 4.08 N: 7.55. Found (%): C: 61.30 H: 4.42 N: 7.10.

N-{[2-(2-Chlorophenyl)-7-fluoroquinolin-4-yl]thioxomethyl}-N-methylglycine. M.p. 168°–172° C. (decompn.).

Elem. Anal. C$_{19}$H$_{14}$ClFN$_2$O$_2$S: Calcd (%): C: 58.69 H: 3.63 N: 7.20. Found (%): C: 58.88 H: 3.86 N: 7.09.

N-[(2-Phenyl-7-fluoroquinolin-4-yl)thioxomethyl]-N-methylglycine. M.p. 221°–223° C. (decompn.).

Elem. Anal. C$_{19}$H$_{15}$FN$_2$O$_2$S: Calcd (%): C: 64.39 H: 4.27 N: 7.90. Found (%): C: 64.54 H: 4.04 N: 7.75.

N-{[2-(2-Chlorophenyl)quinolin-4-yl]thioxomethyl}-N-methylglycine. M.p. 194°–195° C.

Elem. Anal. C$_{19}$H$_{15}$ClN$_2$O$_2$S: Calcd (%): C: 61.54 H: 4.08 N: 4.55. Found (%): C: 61.43 H: 3.84 N: 7.41.

N-[(2-Phenyl-6,8-dichloroquinolin-4-yl)thioxomethyl]-N-methylglycine. M.p. 223°–225° C.

Elem. Anal. C$_{19}$H$_{14}$Cl$_2$N$_2$O$_2$S: Calcd (%): C: 56.31 H: 3.48 N: 7.49. Found (%): C: 56.08 H: 3.71 N: 7.25.

N-{[2-(3-Methylphenyl)quinolin-4-yl]thioxomethyl}-N-methylglycine. M.p. 130° C. (decompn.).

Elem. Anal. C$_{20}$H$_{18}$N$_2$O$_2$S.H$_2$O: Calcd (%): C: 65.20 H: 5.47 N: 7.60. Found (%): C: 54.89 H: 5.18 N: 7.48.

N-[(2-Phenyl-7-chloroquinolin-4-yl)thioxomethyl]-N-methylglycine. M.p. 176°–179° C. (decompn.).

Elem. Anal. C$_{19}$H$_{15}$ClN$_2$O$_2$S: Calcd (%): C: 61.54 H: 4.08 N: 7.55. Found (%): C: 61.42 H: 4.02 N: 7.45.

N-{[2-(2-Fluorohenyl)-7-fluoroquinolin-4-yl]thioxomethyl}-N-methylglycine. M.p. 206°–207° C.

Elem. Anal. C$_{19}$H$_{14}$F$_2$N$_2$O$_2$S: Calcd (%): C: 61.28 H: 3.79 N: 7.52. Found (%): C: 61.59 H: 3.86 N: 7.49.

N-[(2-Phenyl-7-methoxyquinolin-4-yl)thioxomethyl]-N-methylglycine. M.p. 150°–158° C. (decompn.).

Elem. Anal. C$_{20}$H$_{18}$N$_2$O$_3$S: Calcd (%): C: 65.56 H: 4.95 N: 7.64. Found (%): C: 65.23 H: 5.18 N: 7.38.

N-{[2-(2-Chlorophenyl)-7-methoxyquinolin-4-yl]thioxomethyl}-N-methylglycine. M.p. 139°–143° C. (decompn.).

Elem. Anal. C$_{20}$H$_{17}$Cl N$_2$O$_3$S: Calcd (%): C: 59.92 H: 4.27 N: 6.99. Found (%): C: 59.93 H: 4.52 N: 6.70.

N-{[2-(2,4-Dichlorophenyl)-7-methoxyquinolin-4-yl]thioxomethyl}-N-methylglycine. M.p. 141°–146° C. (decompn.).

Elem. Anal. C$_{20}$H$_{16}$Cl$_2$N$_2$O$_3$S: Calcd (%): C: 55.18 H: 3.70 N: 6.44. Found (%): C: 55.49 H: 3.80 N: 6.28.

N-{[2-(2-Fluorophenyl)-7-methoxyquinolin-4-yl]thioxomethyl}-N-methylglycine. M.p. 131°–138° C. (decompn.).

Elem. Anal. $C_{20}H_{17}F N_2O_3S$: Calcd (%): C: 62.49 H: 4.46 N: 7.29. Found (%): C: 62.71 H: 4.69 N: 7.58.

N-[(2-Methylquinolin-4-yl)thioxomethyl]-N-methylglycine. M.p. 140° C. (decompn.).

Elem. Anal. $C_{14}H_{14}N_2O_2S \cdot 3/2H_2O$: Calcd (%): C: 55.80 H: 5.69 N: 9.30. Found (%); C: 55.78 H: 5.36 N: 9.05.

N-[(2-Methyl-8-trifluoromethylquinolin-4-yl)thioxomethyl]-N-methylglycine. M.p. 219°–220° C. (decompn.).

Elem. Anal. $C_{15}H_{13}F_3N_2O_2S$: Cacld (%): C: 52.63 H: 3.83 N: 8.18. Found (%): C: 52.96 H: 3.75 N: 8.16.

N-[(2-Ethyl-8-trifluoromethylquinolin-4-yl)thioxomethyl]-N-methylglycine. M.p. 153°–155° C. (decompn.).

Elem. Anal. $C_{16}H_{15}F_3N_2O_2S$: Calcd (%): C: 53.93 H: 4.24 N: 7.86. Found (%): C: 53.75 H: 4.38 N: 7.80.

N-[(2-Isopropyl-8-trifluoromethylquinolin-4-yl)thioxomethyl]-N-methylglycine. M.p. 137°–139° C.

Elem. Anal. $C_{17}H_{17}F_3N_2O_2S$: Calcd (%): C: 55.13 H: 4.63 N: 7.56. Found (%): C: 54.94 H: 4.51 N: 7.44.

N-[(2-n-Propyl-8-trifluoromethylquinolin-4-yl)thioxomethyl]-N-methylglycine. M.p. 139°–142° C. (decompn.).

Elem. Anal. $C_{17}H_{17}F_3N_2O_2S$: Calcd (%): C: 55.13 H: 4.63 N: 7.56. Found (%): C: 55.50 H: 4.34 N: 7.37.

N-[(2-Isobutyl-8-trifluoromethylquinolin-4-yl)thioxomethyl]-N-methylglycine. M.p. 177°–180° C. (decompn.).

Elem. Anal. $C_{18}H_{19}F_3N_2O_2S$: Calcd (%): C: 56.24 H: 4.98 N: 7.29. Found (%): C: 56.17 H: 4.92 N: 7.06.

N-[(2-Cyclopropyl-8-trifluoromethylquinolin-4-yl)thioxomethyl]-N-methylglycine. M.p. 153°–154° C. (decompn.).

Elem. Anal. $C_{17}H_{15}F_3N_2O_2S$: Calcd (%): C: 55.43 H: 4.10 N: 7.60. Found (%): C: 55.64 H: 4.17 N: 7.46.

N-[(8-{Trifluoromethylquinolin-4-yl)thioxomethyl]-N-methylglycine. M.p. 184°–186° C. (decompn.).

Elem. Anal. $C_{14}H_{11}F_3N_2O_2S$: Calcd (%): C: 51.22 H: 3.38 N: 8.53. Found (%): C: 51.49 H: 3.52 N: 8.46.

N-[(2-methoxyquinolin-4-yl)thioxomethyl]-N-methylglycine. M.p. 118°–120° C.

Elem. Anal. $C_{14}H_{14}N_2O_3S \cdot H_2O$: Calcd (%): C: 54.53 H: 5.23 N: 9.08. Found (%): C: 54.13 H: 4.88 N: 8.94.

N-[(2-Phenoxyquinolin-4-yl)thioxomethyl]-N-methylglycine. M.p. 173°–174° C.

Elem. Anal. $C_{19}H_{16}N_2O_3S$: Cacld (%): C: 64.76 H: 4.58 N: 7.95. Found (%): C: 64.90 H: 4.79 N: 7.91.

beta-Hydroxyethyl ester of N-{[2-(2-hydroxyethoxy)quinolin-4-yl]thioxomethyl}-N-methylglycine. M.p. 106°–107° C.

Elem. Anal. $C_{17}H_{20}N_2O_5S$: Calcd (%): C: 56.03 H: 5.53 N: 7.69. Found (%): C: 55.85 H: 5.52 N: 7.70.

beta-Hydroxyethyl ester of N-[(6,8-dichloro-2-methylquinolin-4-yl)thioxomethyl]-N-methylglycine. M.p. 120°–123° C.

Elem. Anal. $C_{16}H_{16}Cl_2N_2O_3S$: Calcd (%): C: 49.62 H: 4.16 N: 7.23. Found (%): C: 49.54 H: 4.49 N: 7.22.

beta-Hydroxyethyl ester of N-[(2-isopropyl-8-trifluoromethylquinolin-4-yl)thioxomethyl]-N-methylglycine. M.p. 91°–92° C.

Elem. Anal. $C_{19}H_{21}F_3N_2O_3S$: Calcd (%): C: 55.06 H: 5.11 N: 6.76. Found (%): C: 55.21 H: 5.42 N: 6.63.

beta-Hydroxyethyl ester of N-[(2-n-propyl-8-trifluoromethylquinolin-4-yl)thioxomethyl]-N-methylglycine. M.p. 100°–101° C.

Elem. Anal. $C_{19}H_{21}F_3N_2O_3S$: Calcd (%): C: 55.06 H: 5.11 N: 6.76. Found (%): C: 55.25 H: 5.02 N: 6.74.

beta-Hydroxyethyl ester of N-[(2-isobutyl-8-trifluoromethylquinolin-4-yl)thioxomethyl]-N-methylglycine. M.p. 99°–100° C.

Elem. Anal. $C_{20}H_{23}F_3N_2O_3S$: Calcd (%): C: 56.06 H: 5.41 N: 6.54. Found (%): C: 56.13 H: 5.34 N: 6.40.

beta-Hydroxyethyl ester of N-[(2-cyclopropyl-8-trifluoromethylquinolin-4-yl)thioxomethyl]-N-methylglycine. M.p. 101°–103° C.

Elem. Anal. $C_{19}H_{19}F_3N_2O_3S$: Calcd (%): C: 55.33 H: 4.64 N: 6.79. Found (%): C: 55.14 H: 4.86 N: 6.79.

beta-Hydroxyethyl ester of N-[(8-trifluoromethylquinolin-4-yl)thioxomethyl]-N-methylglycine. M.p. 112°–113° C.

Elem. Anal. $C_{16}H_{15}F_3N_2O_3S$: Calcd (%): C: 51.61 H: 4.06 N: 7.52. Found (%): C: 51.81 H: 4.22 N: 7.62.

Ethyl ester of N-[(2-phenylquinolin-4-yl)thioxomethyl]-N-methylglycine. M.p. 139°–140° C.

Elem. Anal. $C_{21}H_{20}N_2O_2S$: Calcd (%): C: 69.21 H: 5.53 N: 7.69. Found (%): C: 69.07 H: 5.68 N: 7.61.

beta-Methoxyethyl ester of N-[(2-phenylquinolin-4-yl)thioxomethyl]-N-methylglycine. M.p. 125°–126° C.

Elem. Anal. $C_{22}H_{22}N_2O_3S$: Calcd (%): C: 66.98 H: 5.62 N: 7.10. Found (%): C: 67.18 H: 5.59 N: 7.01.

beta-Acetoxyethyl ester of N-[(2-phenylquinolin-4-yl)thioxomethyl]-N-methylglycine. M.p. 88°–91° C.

Elem. Anal. $C_{23}H_{22}N_2O_4S$: Calcd (%): C: 65.39 H: 5.25 N: 6.63. Found (%): C: 65.38 H: 5.63 N: 6.59.

beta-N,N-Dimethylaminoethyl ester of N-[(2-phenylquinolin-4-yl)-thioxomethyl]-N-methylglycine. Maleate, M.p. 178°–182° C.

Elem. anal. $C_{27}H_{29}N_3O_6S$: Calcd. (%): C: 61.94 H: 5.58 N: 8.63. Found (%): C: 61.64 H: 5.94 N: 8.43.

2-(2-Hydroxyethoxy) ethyl ester of N-[(2-phenylquinolin-4-yl)-thioxomethyl]-N-methylglycine. M.p. 113°–114° C.

Elem. Anal. $C_{23}H_{24}N_2O_4S$: Calcd (%): C: 65.08 H: 5.70 N: 6.60. Found (%): C: 64.98 H: 5.85 N: 6.55.

2,3-Dihydroxypropyl ester of N-[(2-phenylquinolin-4-yl)-thioxomethyl]-N-methylglycine. M.p. 141°–144° C.

Elem. Anal. $C_{22}H_{22}N_2O_4S$: Calcd (%): C: 64.37 H: 5.40 N: 6.82. Found (%): C: 64.21 H: 5.21 N: 6.77.

beta-Hydroxyethyl ester of N-{[2-(4-methylphenyl)-6-fluoroquinolin-4-yl]thioxomethyl}-N-methylglycine. M.p. 209°–211° C.

Elem. Anal. $C_{22}H_{21}F N_2O_3S$: Calcd (%): C: 64.06 H: 5.13 N: 6.79. Found (%): C: 63.92 H: 5.40 N: 6.70.

Methyl ester of N-{[2-(4-methylphenyl)-6-fluoroquinolin-4-yl]thioxomethyl}-N-methylglycine. M.p. 188°–189° C.

Elem. Anal. $C_{21}H_{19}F N_2O_2S$: Calcd (%): C: 65.95 H: 5.01 N: 7.32. Found (%): C: 66.18 H: 5.23 N: 7.40.

N-{[2-(4-Methylphenyl)-6-fluoroquinolin-4-yl]thioxomethyl}-N-methylglycine. M.p. 230°–235° C.

Elem. Anal. $C_{20}H_{17}F N_2O_2S$: Calcd (%): C: 65.20 H: 4.65 N: 7.60. Found (%): C: 64.89 H: 4.69 N: 7.53.

N-[(2-Phenyl-6-fluoroquinolin-4-yl)thioxomethyl]-N-methylglycine. M.p. 237°–239° C. (decompn.).

Elem. Anal. $C_{19}H_{15}F N_2O_2S$: Calcd (%): C: 64.39 H: 4.27 N: 7.90. Found (%): C: 64.35 H: 4.46 N: 7.73.

N-[(6,8-Dichloro-2-phenylquinolin-4-yl)carbonyl]-N-methylglycine. M.p. 229°–230° C.

Elem. Anal. $C_{19}H_{14}Cl_2N_2O_3$: Calcd (%): C: 58.63 H: 3.63 N: 7.20. Found (%): C: 58.52 H: 3.65 N: 7.23.

Methyl ester of N-[(6,8-dichloro-2-phenylquinolin-4-yl)carbonyl]-N-methylglycine. M.p. 165°–166° C.

Elem. Anal. $C_{20}H_{16}Cl_2N_2O_3$: Calcd (%): C: 59.57 H: 4.00 N: 6.95. Found (%): C: 59.57 H: 4.00 N: 6.93.

beta-Hydroxyethyl ester of N-[(6,8-dichloro-2-phenylquinolin-4-yl)carbonyl]-N-methylglycine. M.p. 186°–189° C.

Elem. Anal. $C_{21}H_{18}Cl_2N_2O_4$: Calcd (%): C: 58.21 H: 4.19 N: 6.47. Found (%): C: 58.02 H: 4.24 N: 6.48.

N-{[(6,8-Dichloro-2-(2-fluorophenyl)quinolin-4-yl]-thioxomethyl}-N-methylglycine. M.p. 205°–207° C. (decompn.).

Elem. Anal. $C_{19}H_{13}Cl_2F\ N_2O_2S$: Calcd (%): C: 53.91 H: 3.10 N: 6.62. Found (%): C: 53.86 H: 3.05 N: 6.69.

N-{[6,8-Dichloro-2-(4-cyclohexylphenyl)quinolin-4-yl]thioxomethyl}-N-methylglycine. M.p. 214°–218° C.

Elem. Anal. $C_{25}H_{24}Cl_2N_2O_2S$: Calcd (%): C: 61.60 H: 4.96 N: 5.75. Found (%): C: 61.41 H: 5.01 N: 5.71.

N-[(7,8-Dichloro-2-phenylquinolin-4-yl)thioxomethyl]-N-methylglycine. M.p. 170°–173° C. (decompn.).

Elem. Anal. $C_{19}H_{14}Cl_2N_2O_3S$: Calcd (%): C: 56.31 H: 3.48 N: 6.91. Found (%): C: 56.05 H: 3.54 N: 7.04.

N-{[7,8-Dichloro-2-(4-methoxyhenyl)quinolin-4-yl]thioxomethyl}-N-methylglycine. M.p. 245°–247° C. (decompn.).

Elem. Anal. $C_{20}H_{16}Cl_2N_2O_3S$: Calcd (%): C: 55.18 H: 3.70 N: 6.43. Found (%): C: 55.19 H: 3.63 N: 6.35.

N-{[7,8-Dichloro-2-(4-methylphenyl)quinolin-4-yl]thioxomethyl}-N-methylglycine. M.p. 224°–225° C.

Elem. Anal. $C_{20}H_{16}Cl_2N_2O_2S$: Calcd (%): C: 57.29 H: 3.85 N: 6.68. Found (%): C: 57.35 H: 3.86 N: 6.68.

N-[(7,8-Dimethyl-2-phenylquinolin-4-yl)thioxomethyl]-N-methylglycine. M.p. 198°–200° C. (decompn.).

Elem. Anal. $C_{21}H_{20}N_2O_2S$: Calcd (%): C: 69.20 H: 5.53 N: 7.69. Found (%): C: 68.99 H: 5.69 N: 7.41.

N-{[7,8-Dimethyl-2-(4-chlorophenyl)quinolin-4-yl]thioxomethyl}-N-methylglycine. M.p. 236°–237° C. (decompn.).

Elem. Anal. $C_{21}H_{19}Cl\ N_2O_2S$: Calcd (%): C: 63.23 H: 4.80 N: 7.02. Found (%): C: 63.29 H: 4.95 N: 7.02.

N-[(8-Chloro-2-phenylquinolin-4-yl)thioxomethyl]-N-methylglycine. M.p. 211°–213° C. (decompn.).

Elem. Anal. $C_{19}H_{15}Cl\ N_2O_2S$: Calcd (%): C: 61.54 H: 4.08 N: 7.55. Found (%): C: 61.41 H: 4.19 N: 7.43.

N-{[8-Chloro-2-(2-methoxyphenyl)quinolin-4-yl]thioxomethyl}-N-methylglycine. M.p. 143°–150° C. (decompn.).

Elem. Anal. $C_{20}H_{17}Cl\ N_2O_3S$: Calcd (%): C: 59.92 H: 4.27 N: 6.99. Found (%): C: 59.71 H: 4.47 N: 6.93.

N-{[6,8-Dichloro-2-(4-isopropylphenyl)quinolin-4-yl]-thioxomethyl}-N-methylglycine. M.p. 133°–137° C. (decompn.).

Elem. Anal. $C_{22}H_{20}Cl_2N_2O_2S$: Calcd (%): C: 59.06 H: 4.51 N: 6.26. Found (%): C: 58.83 H: 4.75 N: 6.01.

N-{[8-Chloro-2-(3-methylphenyl)quinolin-4-yl]thioxomethyl}-N-methylglycine. M.p. 182°–185° C. (decompn.).

Elem. Anal. $C_{20}H_{17}Cl\ N_2O_2S$: Calcd (%): C: 62.41 H: 4.45 N: 7.29. Found (%): C: 62.46 H: 4.69 N: 7.00.

N-[(2-Phenyl-6-isopropylquinolin-4-yl)thioxomethyl]-N-methylglycine. M.p. 226°–227° C. (decompn.).

Elem. Anal. $C_{22}H_{22}N_2O_2S$: Calcd (%): C: 69.81 H: 5.86 N: 7.40. Found (%): C: 69.84 H: 6.08 N: 7.35.

N-{[2-(4-Cyclohexylphenyl)-8-trifluoromethylquinolin-4-yl]thioxomethyl}-N-methylglycine. M.p. 252°–254° C. (decompn.).

Elem. Anal. $C_{26}H_{25}F_3N_2O_2S$: Calcd (%): C: 64.18 H: 5.18 N: 5.76. Found (%): C: 64.19 H: 5.23 N: 5.72.

N-{[2-(4-n-Hexylphenyl)-6-isopropylquinolin-4-yl]thioxomethyl}-N-methylglycine. M.p. 167°–169° C. (decompn.).

Elem. Anal. $C_{28}H_{34}N_2O_2S$: Calcd (%): C: 72.69 H: 7.41 N: 6.05. Found (%): C: 72.47 H: 7.43 N: 5.94.

N-{[2-(4-Chlorophenyl)-6-isopropylquinolin-4-yl]thioxomethyl}-N-methylglycine. M.p. 224°–228° C.

Elem. Anal. $C_{22}H_{21}Cl\ N_2O_2S$: Calcd (%): C: 63.99 H: 5.13 N: 6.78. Found (%): C: 63.92 H: 5.22 N: 6.71.

N-{[2-(4-Chlorophenyl)-6-isopropylquinolin-4-yl]carbonyl}-N-methylglycine. M.p. 186°–188° C.

Elem. Anal. $C_{22}H_{21}Cl\ N_2O_3$: Calcd (%): C: 66.58 H: 5.33 N: 7.06. Found (%): C: 66.29 H: 5.59 N: 6.92.

TEST EXAMPLE

As hereunder, the result of pharmacological test of the representative compounds of the present invention is given.

Test Method (A) Activity of aldose reductase was measured by a method disclosed in S. Hayman and J. H. Kinoshita: J. Biol. Chem., 240, 877, 1965. The aldose reductase used was that obtained from crystal eye of cow and the measurement was done in vitro. The result is given in Table 1.

(B) Male rats of Sprague-Dawley strain (body weight: 150 to 200 g) were fasted overnight and used in the test (one group comprised 4 rats). To all groups were given 5 g/kg of galactose orally, then the rats were sacrificed after 3 hours, and sciatic nerve was taken out and weighed. The content of galactitol in the sciatic nerve was measured by high performance liquid chromatography in accordance with a method by Jean-Marie Dethy (Anal. Biochem. 143, 119, 1984). The test compound was given orally 4 hours prior to the administration of galactose. To the control group was given 0.5% methylcellulose. The result is given in Table 2.

(C) Non-fasted male rats of Sprague-Dawley strain (5 rats in one group) of 150–220 g body weight were used. To all groups was administered 20% galactose diet (a mixture of galactose and F-2 which is a product of Funahashi Farm) and fed for 4 days. The test compound was given orally at 9 a.m. and 5 p.m. from the first to the fourth day. On the fifth day, the rats were sacrificed, sciatic nerve was taken out, and the amounts of inositol and galactitol in the sciatic nerve were measured by the method as given before. The result is given in Table 3.

It is apparent that the present invention compounds exhibit pharmacological activity out of the Tables 1, 2 and 3.

TABLE 1

| Compound No. | $IC_{50}$ (moles) |
|---|---|
| 1 | $>8.7 \times 10^{-6}$ |
| 2 | $>8.7 \times 10^{-6}$ |
| 3 | $>8.7 \times 10^{-6}$ |
| Tolrestat | $7.3 \times 10^{-9}$ |

The compound numbers correspond to the following compounds of the present invention:

1: β-Hydroxyethyl ester of N-[(2-phenylquinolin-4-yl)thioxomethyl]-N-methylglycine.

2: β-Hydroxyethyl ester of N-[(2-methyl-8-trifluoromethylquinolin-4-yl)thioxomethyl]-N-methylglycine.

3: β-Hydroxyethyl ester of N-[{2-(2-fluorophenyl)-7-fluoroquinolin-4-yl)}thioxomethyl]-N-methylglycine.

TABLE 2

| Compound | Inhibition rate (%) against Accumulation of Galactitol in sciatic nerve. Dose (mg/kg) | | | |
|---|---|---|---|---|
| | 100 | 50 | 20 | 10 |
| 1 | 92.57 | 84.57 | 54.88 | |
| 2 | | 98.19 | 91.28 | 45.37 |
| 3 | | 70.78 | 32.68 | |
| 5 | | 79.66 | 13.98 | |
| Tolrestat | 95.43 | 68.00 | 28.26 | 21.01 |

5: β-Hydroxyethyl ester of N-[(2-ethyl-8-trifluoromethylquinolin-4-yl)thioxomethyl]-N-methylglycine.

TABLE 3

| Compound | Inhibition Rate (%) Dose | | |
|---|---|---|---|
| | 5 | 10 | 20 mg/kg |
| 1 | | 45 | 67 |
| 2 | 27 | 46 | 77 |
| 3 | | 26 | 37 |
| Tolrestat | 34 | 86 | 96 |

Acute Toxicity

Male mice of ddY strain (5 weeks of age) were used (one group comprised 4 to 5 mice). The test drug suspended in 0.5% methylcellulose of physical saline was orally given, then usual feeding was done, and the general symptom and the status of death or alive were observed for two weeks. The rate of death is given in Table 4.

TABLE 4

| Compound | 500 | 1000 mg/kg |
|---|---|---|
| 1 | | 0/4 |
| 3 | | 0/4 |
| 5 | | 0/4 |
| Tolrestat | 2/4 | 3/4 |

Thus, all of the present invention compounds tested were with low toxicity and no abnormal change was observed by administration of 1 g/kg. Even by administration of 3 g/kg, there was no case of death with reference to the compound 1.

(Effect)

It is apparent from the above-given results that the present invention compounds inhibit an accumulation of galactitol, exhibit marked aldose reductase inhibiting action with low toxicity, and can be safely used as agents for prevention and therapy of diabetic complications such as nervous hindrance, renal and retinal diseases, and cataract.

We claim:

1. A compound of the formula (I):

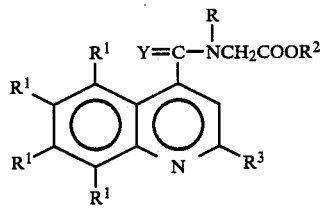

(I)

or a pharmaceutically acceptable salt thereof wherein Y is S;

R is hydrogen or alkyl having from about 1 to about 4 carbon atoms;

$R^1$ is independently hydrogen, alkyl having from about 1 to about 4 carbon atoms, alkoxy having from about 1 to about 4 carbon atoms, halogen or trifluoromethyl;

$R^2$ is hydrogen or alkyl having from about 1 to about 4 carbon atoms optionally substituted by hydroxyl, alkoxy having from about 1 to about 4 carbon atoms, hydroxyalkoxy having from about 1 to about 4 carbon atoms, acyloxy having from about 1 to about 4 carbon atoms, amino or alkyl- or dialkylamino having from about 1 to about 4 carbon atoms in the alkyl moiety; and $R^3$ is hydrogen, alkyl having from about 1 to about 6 carbon atoms, cycloalkyl having from about 3 to about 6 carbon atoms, alkoxy having from about 1 to about 4 carbon atoms, aryloxy having from about 6 to about 10 carbon atoms, alkylthio having from about 1 to about 4 carbon atoms, hydroxyalkoxy having from about 1 to about 4 carbon atoms, or phenyl optionally substituted by one to three substituents selected from the group consisting of alkyl having from about 1 to about 8 carbon atoms, cycloalkyl having from about 3 to about 6 carbon atoms, alkoxy having from about 1 to about 4 carbon atoms, halogen and trifluoromethyl.

2. The compound according to claim 1, which is betahydroxyethyl ester of N-[2-phenylquinolin-4-yl)-thioxomethyl]-N-methylglycine or a pharmaceutically acceptable salt thereof.

3. The compound according to claim 1, which is betahydroxyethyl ester of N-[2-methyl-8-trifluoromethylquinolin-4-yl)-thioxomethyl]-N-methylglycine or a pharmaceutically acceptable salt thereof.

4. The compound according to claim 1, which is betahydroxyethyl ester of N-[{2-(2-fluorophenyl)-7-fluoroquinolin-4-yl}-thioxomethyl]-N-methylglycine or a pharmaceutically acceptable salt thereof.

5. The compound according to claim 1, which is betahydroxyethyl ester of N-[(2,6-dimethylquinolin-4-yl)thioxomethyl]-N-methylglycine or a pharmaceutically acceptable salt thereof.

6. The compound according to claim 1, which is N-[2-phenyl-6-chloroquinolin-4-yl)-thioxomethyl]-N-methylglycine or a pharmaceutically acceptable salt thereof.

7. The compound according to claim 1, which is N-{[2-(4-methylphenyl)-6-fluoroquinolin-4-yl]thioxomethyl}-N-methylglycine or a pharmaceutically acceptable salt thereof.

8. The compound according to claim 1, which is betahydroxyethyl ester of N-[(2-ethyl-8-trifluoromethylquinolin-4-yl)thioxomethyl]-N-methylglycine.

9. A pharmaceutical composition useful for the prevention and treatment of diabetic complications in animals, including humans which comprises an aldose reductase inhibition effective amount of a compound of the formula (I):

$$R^1 \underset{R^1}{\underset{|}{\overset{R}{\diagup}}} \overset{R}{\underset{N}{\diagdown}} \overset{Y=C-NCH_2COOR^2}{\underset{R^3}{\diagup}} \quad (I)$$

or a pharmaceutically acceptable salt thereof wherein
Y is S;
R is hydrogen or alkyl having from about 1 to about 4 carbon atoms;
$R^1$ is independently hydrogen, alkyl having from about 1 to about 4 carbon atoms, alkoxy having from about 1 to about 4 carbon atoms, halogen or trifluoromethyl;
$R^2$ is hydrogen or alkyl having from about 1 to about 4 carbon atoms optionally substituted by hydroxyl, alkoxy having from about 1 to about 4 carbon atoms, hydroxyalkoxy having from about 1 to about 4 carbon atoms, acyloxy having from about 1 to about 4 carbon atoms, amino or alkyl- or dialkylamino having from about 1 to about 4 carbon atoms in the alkyl moiety; and
$R^3$ is hydrogen, alkyl having from about 1 to about 6 carbon atoms, cycloalkyl having from about 3 to about 6 carbon atoms, alkoxy having from about 1 to about 4 carbon atoms, aryloxy having from about 6 to about 10 carbon atoms, alkylthio having from about 1 to about 4 carbon atoms, hydroxyalkoxy having from about 1 to about 4 carbon atoms, or phenyl optionally substituted by one to three substituents selected from the group consisting of alkyl having from about 1 to about 8 carbon atoms, cycloalkyl having from about 3 to about 6 carbon atoms, alkoxy having from about 1 to about 4 carbon atoms, halogen and trifluoromethyl, in combination with a pharmaceutically acceptable carrier or diluent thereof.

10. A method for inhibiting aldose reductase in animals, including humans, which comprises administering to an animal including humans, in need thereof an aldose reductase inhibition effective amount of a compound of the formula (I):

$$R^1 \underset{R^1}{\underset{|}{\overset{R}{\diagup}}} \overset{R}{\underset{N}{\diagdown}} \overset{Y=C-NCH_2COOR^2}{\underset{R^3}{\diagup}} \quad (I)$$

or a pharmaceutically acceptable salt thereof, wherein
Y is S
R is hydrogen or alkyl having from about 1 to about 4 carbon atoms;
$R^1$ is independently hydrogen, alkyl having from about 1 to about 4 carbon atoms, alkoxy having from about 1 to about 4 carbon atoms, halogen or trifluoromethyl;
$R^2$ is hydrogen or alkyl having from about 1 to about 4 carbon atoms optionally substituted by hydroxyl, alkoxy having from about 1 to about 4 carbon atoms, hydroxyalkoxy having from about 1 to about 4 carbon atoms, acyloxy having from about 1 to about 4 carbon atoms, amino or alkyl- or dialkylamino having from about 1 to about 4 carbon atoms in the alkyl moiety; and
$R^3$ is hydrogen, alkyl having from about 1 to about 6 carbon atoms, cycloalkyl having from about 3 to about 6 carbon atoms, alkoxy having from about 1 to about 4 carbon atoms, aryloxy having from about 6 to about 10 carbon atoms, alkylthio having from about 1 to about 4 carbon atoms, hydroxyalkoxy having from about 1 to about 4 carbon atoms, or phenyl optionally substituted by one to three substituents selected from the group consisting of alkyl having from about 1 to about 8 carbon atoms, cycloalkyl having from about 3 to about 6 carbon atoms, alkoxy having from about 1 to about 4 carbon atoms, halogen and trifluoromethyl.

11. The method according to claim 10, wherein said compound is beta-hydroxyethyl ester of N-[(2-phenylquinolin-4-yl)thioxomethyl]-N-methylglycine or a pharmaceutically acceptable salt thereof.

12. The method according to claim 10, wherein said compound is beta-hydroxyethyl ester of N-[(2-methyl-8-trifluoromethylquinolin-4-yl)-thioxomethyl]-N-methylglycine or a pharmaceutically acceptable salt thereof.

13. The method according to claim 10, wherein said compound is beta-hydroxyethyl ester of N-[{2-(2-fluorophenyl)-7-fluoroquinolin-4-yl}-thioxomethyl]-N-methylglycine or a pharmaceutically acceptable salt thereof.

14. The method according to claim 10, wherein said compound is beta-hydroxyethyl ester of N-[(2,6-dimethylquinolin-4-yl)thioxomethyl]-N-methylglycine or a pharmaceutically acceptable salt thereof.

15. The method according to claim 10, wherein said compound is N-[2-phenyl-6-chloroquinolin-4-yl)-thioxomethyl]-N-methylglycine or a pharmaceutically acceptable salt thereof.

16. The method according to claim 10, wherein said compound is N-{[2-(4-methylphenyl)-6-fluoroquinolin-4-yl]thioxomethyl}-N-methylglycine or a pharmaceutically acceptable salt thereof.

17. The method according to claim 10, wherein said compound is beta-hydroxyethyl ester of N-[(2-ethyl-8-trifluoromethylquinolin-4-yl)thioxomethyl]-N-methylglycine.

18. A method for the prevention and/or treatment of diabetic complications in animals, including humans, which comprises administering to an animal, including humans, in need thereof an aldose reductase inhibition effective amount of a compound of the formula (I):

$$R^1 \underset{R^1}{\underset{|}{\overset{R}{\diagup}}} \overset{R}{\underset{N}{\diagdown}} \overset{Y=C-NCH_2COOR^2}{\underset{R^3}{\diagup}} \quad (I)$$

or a pharmaceutically acceptable salt thereof, wherein
Y is S
R is hydrogen or alkyl having from about 1 to about 4 carbon atoms;

$R^1$ is independently hydrogen, alkyl having from about 1 to about 4 carbon atoms, alkoxy having from about 1 to about 4 carbon atoms, halogen or trifluoromethyl;

$R^2$ is hydrogen or alkyl having from about 1 to about 4 carbon atoms optionally substituted by hydroxyl, alkoxy having from about 1 to about 4 carbon atoms, hydroxyalkoxy having from about 1 to about 4 carbon atoms, acyloxy having from about 1 to about 4 carbon atoms, amino or alkyl- or dialkyl-amino having from about 1 to about 4 carbon atoms in the alkyl moiety; and $R^3$ is hydrogen, alkyl having from about 1 to about 6 carbon atoms, cycloalkyl having from about 3 to about 6 carbon atoms, alkoxy having from about 1 to about 4 carbon atoms, aryloxy having from about 6 to about 10 carbon atoms, alkylthio having from about 1 to about 4 carbon atoms, hydroxyalkoxy having from about 1 to about 4 carbon atoms, or phenyl optionally substituted by one to three substituents selected from the group consisting of alkyl having from about 1 to about 8 carbon atoms, cycloalkyl having from about 3 to about 6 carbon atoms, alkoxy having from about 1 to about 4 carbon atoms, halogen and trifluoromethyl.

19. A composition according to claim 9, wherein the compound is the betahydroxyethyl ester of N-[2-phenylquinolin-4-yl)thioxomethyl]-N-methylglycine or a pharmaceutically acceptable salt thereof.

20. A composition according to claim 9, wherein the compound is the beta-hydroxyethyl ester of N-[2-methyl-8-trifluoromethylquinolin-4-yl)-thioxomethyl]-N-methylglycine or a pharmaceutically acceptable salt thereof.

21. A composition according to claim 9, wherein the compound is the beta-hydroxyethyl ester of N-[{2-(2-fluorophenyl)-7-fluoroquinolin-4-yl}-thioxomethyl]-N-methylglycine or a pharmaceutically acceptable salt thereof.

22. A composition according to claim 9, wherein the compound is the beta-hydroxyethyl ester of N-[(2,6-dimethylquinolin-4-yl) thioxomethyl]-N-methylglycine or a pharamaceutically acceptable salt thereof.

23. A composition according to claim 9, wherein the compound is N-[2-phenyl-6-chloroquinolin-4-yl)-thioxomethyl]-N-methylglycine or a pharmaceutically acceptable salt thereof.

24. A composition according to claim 9, wherein the compound is N-{[2-(4-methyphenyl)-6-fluoroquinolin-4-yl]thioxomethyl}-N-methylglycine or a pharmaceutically acceptable salt thereof.

25. A composition according to claim 9, wherein the compound is the beta-hydroxyethyl ester of N-[(2-ethyl-8-trifluoromethylquinolin-4-yl)thioxomethyl]-N-methylglycine.

26. The method according to claim 18, wherein the compound is the beta-hydroxyethyl ester of N-[(2-phenylquinolin-4-yl)thioxomethyl]-N-methylglycine or a pharmaceutically acceptable salt thereof.

27. The method according to claim 18, wherein the compound is the beta-hydroxyethyl ester of N-[(2-methyl-8-trifluoromethylquinolin-4-yl)-thioxomethyl[-N-methylglycine or a pharmaceutically acceptable salt thereof.

28. The method according to claim 18, wherein the compound is the beta-hydroxyethyl ester of N-[{2-(2-fluorophenyl)-7-fluoroquinolin-4-yl}-thioxomethyl]-N-methylglycine or a pharmaceutically acceptable salt thereof.

29. The method according to claim 18, wherein the compound is the beta-hydroxyethyl ester of N-[(2,6-dimethylquinolin-4-yl)thioxomethyl]-N-methylglycine or a pharmaceutically acceptable salt thereof.

30. The method according to claim 18, wherein the compound is N-[2-phenyl-6-chloroquinolin-4-yl)-thioxomethyl]-N-methyl-glycine or a pharmaceutically acceptable salt thereof.

31. The method according to claim 18, wherein the compound is N-{[2-(4-methylphenyl)-6-fluoroquinolin-4-yl]thioxomethyl}-N-methylglycine or a pharmaceutically acceptable salt thereof.

32. The method according to claim 18, wherein the compound is the beta-hydroxyethyl ester of N-[(2-ethyl-8-trifluoromethylquinolin-4-yl)thioxomethyl]-N-methylglycine.

* * * * *